United States Patent
Durand et al.

(10) Patent No.: US 9,452,927 B2
(45) Date of Patent: Sep. 27, 2016

(54) NANOFLUIDIC BIOSENSOR AND ITS USE FOR RAPID MEASUREMENT OF BIOMOLECULAR INTERACTIONS IN SOLUTION AND METHODS

(75) Inventors: Nicolas Durand, Blonay (CN); Yannick Fournier, Ecublens (CH); Theo Lasser, Denges (CH); Iwan Märki, Yverdon (CH)

(73) Assignee: ECOLE POLYTECHNIQUE FEDERALE DE LAUSANNE (EPFL), Lausanne (CH)

(*) Notice: Subject to any disclaimer, the term of this patent is extended or adjusted under 35 U.S.C. 154(b) by 0 days.

(21) Appl. No.: 13/511,805

(22) PCT Filed: Nov. 19, 2010

(86) PCT No.: PCT/IB2010/055305
§ 371 (c)(1),
(2), (4) Date: Sep. 27, 2012

(87) PCT Pub. No.: WO2011/064701
PCT Pub. Date: Jun. 3, 2011

(65) Prior Publication Data
US 2013/0017967 A1 Jan. 17, 2013

(30) Foreign Application Priority Data

Nov. 27, 2009 (CH) ........................... 1824/09

(51) Int. Cl.
*G01N 33/558* (2006.01)
*B82Y 15/00* (2011.01)
(Continued)

(52) U.S. Cl.
CPC .............. *B82Y 15/00* (2013.01); *B01L 3/5027* (2013.01); *B82Y 35/00* (2013.01); *G01N 21/6452* (2013.01)

(58) Field of Classification Search
CPC ... G01F 1/66; G01F 1/661; G01N 2013/003; G01N 2011/0046; G01N 2012/0112; G01N 2021/59; G01N 2021/751; G01N 2021/752; G01N 2021/754; G01N 2021/755; G01N 21/01; G01N 13/00; G01N 13/04; G01N 11/04; G01N 21/6447
See application file for complete search history.

(56) References Cited

U.S. PATENT DOCUMENTS

| 6,720,177 B2 | 4/2004 | Ghadiri et al. |
| 2006/0160209 A1 | 7/2006 | Larson et al. |

(Continued)

FOREIGN PATENT DOCUMENTS

| CN | 1956678 A | 5/2007 |
| EP | 0 545 284 B1 | 6/1993 |

(Continued)

OTHER PUBLICATIONS

Durand, N. et al 2009 (ePub Dec. 14, 2008) Anal Bioanal Chem 394: 421-425.*
International Search Report for PCT/IB2010/055305, mailed Apr. 29, 2011.
Written Opinion of the International Searching Authority for PCT/IB2010/055305, mailed Apr. 29, 2011.
(Continued)

*Primary Examiner* — Chris L Chin
(74) *Attorney, Agent, or Firm* — Nixon & Vanderhye P.C.

(57) ABSTRACT

A method and device for the rapid detection of biomolecules (320) diffusing in a nanometer-confined slit (204) is claimed. In particular, the present invention relates to a novel concept of fluidic side apertures (205) that facilitates the filling of the device, the surface coating with biomolecules and that measures the affinity between fluorescently labeled biomolecules in aqueous solution with other biomolecules immobilized on surfaces.

22 Claims, 2 Drawing Sheets

(51) Int. Cl.
 *B01L 3/00* (2006.01)
 *B82Y 35/00* (2011.01)
 *G01N 21/64* (2006.01)

(56) References Cited

U.S. PATENT DOCUMENTS

| | | |
|---|---|---|
| 2006/0272433 A1 | 12/2006 | Yamamichi |
| 2007/0020779 A1 | 1/2007 | Stavis et al. |
| 2009/0190129 A1 | 7/2009 | Yguerabide et al. |
| 2009/0214392 A1 | 8/2009 | Kameoka et al. |
| 2009/0221891 A1 | 9/2009 | Yu et al. |
| 2010/0159462 A1 | 6/2010 | Takayama et al. |
| 2010/0267158 A1* | 10/2010 | Chou ............. B01L 3/502761 436/94 |

FOREIGN PATENT DOCUMENTS

| | | |
|---|---|---|
| EP | 1 250 954 A2 | 10/2002 |
| EP | 1 542 010 | 6/2005 |
| JP | 2003-130883 | 5/2003 |
| JP | 2009-8690 | 1/2009 |
| WO | WO 2008/134363 | 11/2008 |

OTHER PUBLICATIONS

Japanese Patent Office Action dated Apr. 2, 2014 and its English translation, for Japanese Patent Application No. 2012-540523 that corresponds to Applicant's PCT/IB2010/055305, filed on Nov. 19, 2010.

Japanese Office Action dated Aug. 12, 2014 issued in Japanese Patent Application No. 2012-540523 and Entlish translation, 7 pp.

Humphreys, Tim, et al, Journal of Micromechanics and Microengineering, vol. 19 (2009) 105024, pp. 1-9, "World-to-chip interconnects for efficient loading of genomic DNA into microfluidic channels.".

Jo, Kyubong, et al, *PNAS*, Feb. 20, 2007, vol. 104, No. 8, pp. 2673-2678, "A single-molecule barcoding system using nanoslits for DNA analysis," (XP-002630573).

Lin, Po-Keng, et al, *Macromolecules*, vol. 42, No. 5, 2009, pp. 1770-1774, "One-Dimensional Dynamics and Transport of DNA Molecules in a Quasi-Two-Dimensional Nanoslit," (XP-002630572).

Baldini et al, Analytical and Bioanalytical Chemistry, vol. 391, No. 5, (Feb. 15, 2008), pp. 1837-1844, "A new optical platform for biosensing based on fluorescence anisotropy."

* cited by examiner

A)

B)

NANOFLUIDIC BIOSENSOR AND ITS USE FOR RAPID MEASUREMENT OF BIOMOLECULAR INTERACTIONS IN SOLUTION AND METHODS

This application is the U.S. national phase of International Application No. PCT/IB2010/055305, filed 19 Nov. 2010, which designated the U.S. and claims priority to CH Application No. 01824/09, filed 27 Nov. 2009, the entire contents of each of which are hereby incorporated by reference.

FIELD OF INVENTION

The present invention relates to methods and devices for the detection of fluorescently labeled biomolecules in nanofluidic biosensors, using an optical set-up. The present invention may advantageously be used for biomedical and biological analyses.

BACKGROUND OF THE INVENTION

Nanofluidics is defined as fluidic systems with channels in the nanometer range size, and has been applied in microfluidic systems allowing for DNA manipulation, protein separation and sample preconcentration. A majority of the current nanofluidic developments are intended for bioengineering and biotechnology applications.

Current practices for the detection of specific biomolecules can be divided in two categories: (a) the labeled techniques and (b) the label-free techniques.

Among the labeled techniques, the widely used are fluorescence, colorimetry, radioactivity, phosphorescence, bioluminescence and chemiluminescence. Functionalized magnetic beads can also be considered as labeling techniques. Their advantages are the sensitivity in comparison to label-free methods and the molecular recognition due to specific labeling.

Among the label-free techniques, the widely used are electrochemical biosensors, referring to amperometric, capacitive, conductometric or impedimetric sensors, which have the advantage of being rapid and inexpensive. They measure the change in electrical properties of electrode structures as biomolecules become entrapped or immobilized onto or near the electrode, but all these concepts lack molecular specific contrast, sensitivity and reliability.

Surface plasmon resonance (SPR) is also a label-free optical technique for monitoring biomolecular interactions occurring in very close vicinity of a transducer gold surface, and has lead to great potential for real-time studying surface-confined affinity interactions without rinsing out unreacted or excess reactants in sample solutions.

Enzyme linked immunosorbent assay (ELISA) is an important biochemical technique mainly used to detect the presence of antibodies and antigens, and thus is widely used as diagnostic tool in medicine and quality control check in various industries. ELISA analysis are however expensive, require large amounts of solution and a long time to obtain results.

OBJECTIVES

It is an object of this invention to provide an inexpensive and rapid biosensor based on micro- and nanofluidics, which does not require complex manipulations.

Still another object of the invention is to geometrically confine the optical measurement volume using nanofluidics and thus to obtain a high sensitivity of the biosensor.

Still another object of the invention is to simplify the different surface coatings compared to existing biosensors.

These and other objects of the present invention will become increasingly apparent with reference to the following drawings and preferred embodiments.

SUMMARY OF THE INVENTION

This invention is based on the discovery that apertures can be designed on the sides of micro- and nanofluidics systems, avoiding thereby complex connections between reservoirs of the fluidic systems and external tubing. The device is filled by simple immersion inside a solution containing the biomolecules to assay. It gives the possibility to measure the interaction between diffusing biomolecules and other biomolecules immobilized on surfaces.

This invention is also based on the discovery that the immersion water usually used with water immersion objectives may also be replaced by a solution containing a small concentration of fluorescent biomolecules to assay if necessary.

Finally, this invention highlights the possibility to functionalize every single die with different biomolecules and to dispose these dies in an array configuration in order to perform rapid multiplexed tests.

In the scope of this invention, nanofluidics is used because of its high surface-to-volume ratio, meaning that the surfaces are included in the detection volume, maximizing the detection of the interactions between diffusing biomolecules and other immobilized biomolecules on surfaces.

DETAILED DESCRIPTION OF THE INVENTION

As used herein, the term "biomolecules" is intended to be a generic term, which includes for example (but not limited to) polyclonal antibodies, monoclonal antibodies, Fab fragments, recombinant antibodies, globular proteins, amino acids, nucleic acids, enzymes, lipid molecules, polysaccharides and virus.

As used herein, the term "nanoslit" is intended to be a generic term, which means well-defined microfabricated structure with a nanometer-sized height, of which the width and the length are larger. The nanometer-sized height of the nanoslit is defined to be higher than 2 nm because of the size of the smallest proteins to detect, that have to enter into the slit and are in the same order of magnitude. The present invention is limited to nanoslits with a height lower than the micron, because of the range of the detection volume of the optical system that are typically in the same order of magnitude.

As used herein, the term "nanochannel" is intended to be a generic term, which means well-defined microfabricated structure with a nanometer-sized height and width, of which the length is larger.

Figure 1:
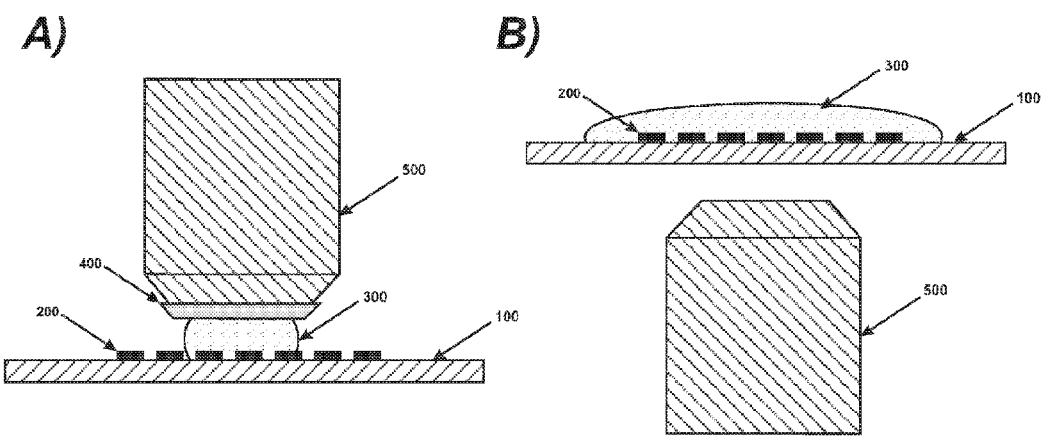
FIG. 1A is a schematic of the system composed of a support 100 on which is attached an array of nanofluidic biosensors 200. A solution containing the fluorescent biomolecules 300 is deposited on the devices and a optical system 500, covered with a contamination filter 400, is used for the measurement.
FIG. 1B is a schematic of an alternative of the biosensing system composed of a support 100 on which is attached an array of nanofluidic devices 200. A solution containing the fluorescent biomolecules 300 is deposited on the devices and a optical system 500, is used in epi-detection.

The present invention aims to simplify the measurement of the presence and of the interaction of specific diffusing biomolecules with surfaces, or with other biomolecules immobilized on surfaces. As shown in FIG. 1, an array of nanofluidic devices 200 is fixed on a support 100, such as standard microscope cover glass or plastic capsule for example. An aqueous solution containing fluorescently labeled biomolecules is disposed on the support, so that at least one of the lateral apertures 205 of the nanofluidic device is included in the solution 300, which results in filling its channels. If necessary and as highlighted in FIG. 1A, a water-immersion microscope objective 500, on which a contamination filter 400 is previously fixed, can be put in contact with the solution. Otherwise, as depicted in FIG. 1B, the optical system is used in epi-detection.

Figure 2:
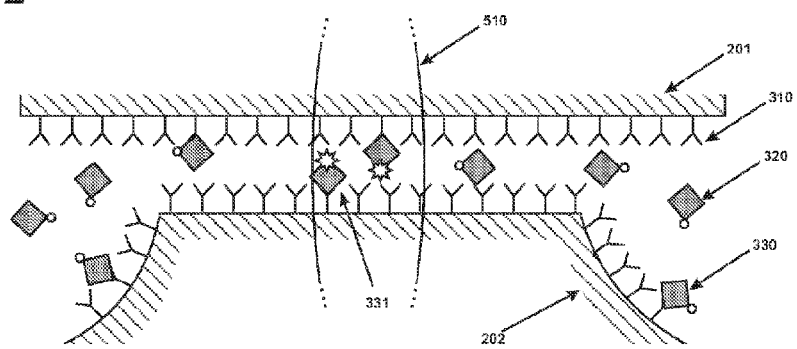
FIG. 2 shows a cross section of the nanoslit defined by two substrates 201 and 202. The intersection between the optical volume 510 and the nanoslit 204 delimits the zone of detection of fluorescent biomolecules 331. Diffusing fluorescent biomolecules 320 may interact with immobilized biomolecules on surface 310, and thus create molecular complexes 330 when a specific binding exists.
Figure 3:
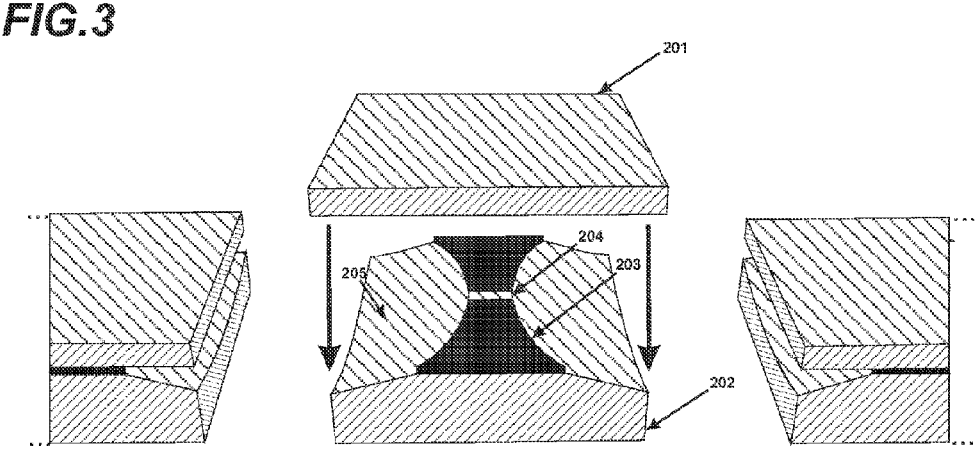
FIG. 3 is a perspective view of an array of microfabricated device composed of a bottom structure 202, on which is deposited a layer of amorphous silicon 203 defining one or several nanoslits 204. A substrate cover 201 is affixed by anodic bonding. The liquid enters in the device from the lateral apertures on the sides 205.

FIG. 2 illustrates the principle of detection and FIG. 3 illustrates the structure of an embodiment of a biosensor according to the invention. First, biomolecules 310 are fixed on surfaces of substrates 201 and 202. The detection volume 510 has to be focused inside a nanoslit 204 in a way that the intersection volume defined by the volume of the nanoslit 204 and the detection volume 510 is maximal. Then, the solution 300 containing the fluorescently labeled biomolecules 320 is filled into the system by capillarity. The biomolecules 320 diffuse and interact with those 310 fixed inside the nanoslit 204 and may create a molecular complex 330, 331. The immobilized fluorescently emitting complexes 331 and the diffusing fluorescently emitting biomolecules 320 diffusing across the optical detection volume are both detected by the optical system.

The present invention is distinguishable from biosensors currently being used to detect molecules interactions. The unique design of side apertures allows the liquid solution to directly enter the fluidic system. This is different from current biosensors based on micro- and nanofluidics reservoirs, which have to be mechanically connected with flexible tubes. Those solutions require injecting the solution containing the biomolecules to analyze, and require driving them through micro- or nanochannels, increasing the manipulation complexity of the system.

The biosensor illustrated on FIG. 3 may be manufactured as follows: First, the lateral apertures of a wafer 202 are etched by wet or dry etching. Then, an amorphous silicon layer 203 of thickness from 2 to 1,000 nm is deposited and structured using standard photolithography techniques, allowing definition of the nanoslit 204 geometry. A second wafer 201 is anodically bonded onto the first wafer 202. The height of this second wafer 201 has to be compatible with the microscope objective. Afterwards, the wafers 201, 202 are diced into individual dies. The nanoslit 204 is linking the two side apertures 205 and is defined by the spacing between the two wafers 201, 202. The amorphous silicon layer 203 is acting as spacer to define the nano slit 204 height.

Figure 4:
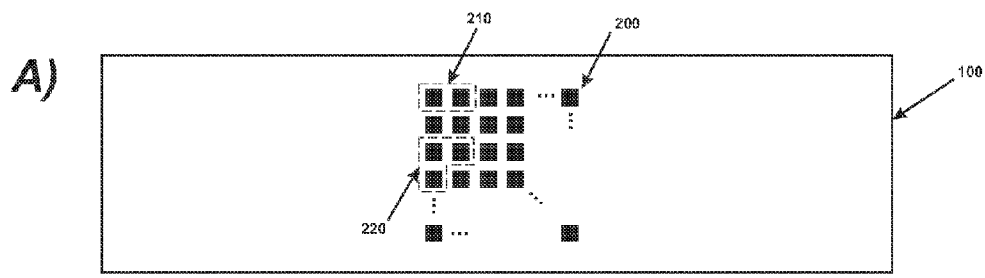
FIG. 4 represents a top view of a support 100, on which is fixed an array of nanofluidic devices 200. (A) illustrates a rectangular array showing for example a 2-die arrangement 210 and a 3-die arrangement 220, and (B) illustrates an hexagonal array showing for example a 3-die arrangement 230 or a 4-die arrangement 240.
Figure 4:
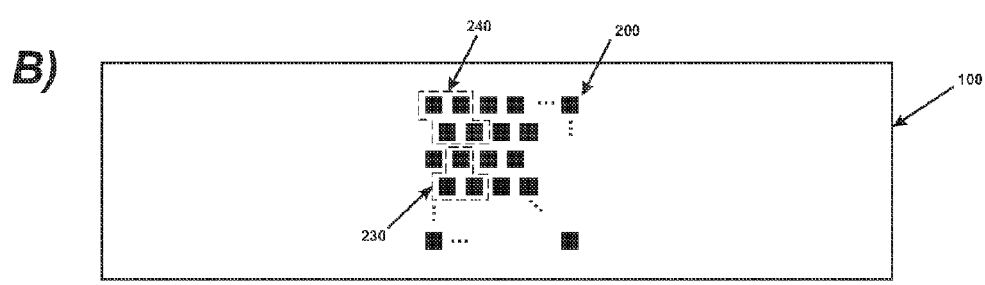

FIG. 4 shows an array of biosensors 200 that are fixed onto the microscope-mountable support 100. The disposition of the biosensors 200 may be (A) rectangular or (B) hexagonal, but any other form can be contemplated.

The handling of the device according to the present invention shows great promise for the detection, enumeration, identification and characterization of the biomolecules interacting or not with other immobilized biomolecules. Applications of the present invention can cover biomedical, biological and food analysis as well as fundamental studies in analytical and bioanalytical chemistry.

The invention claimed is:

1. A biosensor for detecting and measuring interactions of fluorescently labeled biomolecules, said biosensor consisting essentially of a substrate having an upper part designed to be located in front of an optical system, a lower part, and at least two lateral apertures having a specific design, said biosensor further comprising a space for a solution containing biomolecules,
   wherein said space is a nanoslit which is defined between said upper part and lower part and which communicates with the lateral apertures, wherein the at least two lateral apertures have an area from 100 nm$^2$ to 20 mm$^2$ and the nanoslit has a height between 2 nm and 1000 nm, a width between 2 nm and 20 mm, and a length between 2 nm and 20 mm, and wherein the design of the at least two lateral apertures allows the solution to directly enter into the nanoslit by capillarity, without being mechanically injected into the nanoslit.

2. Biosensor according to claim 1 wherein the nanoslit has internal walls, and the internal walls of the nanoslit are pre-coated with a substance, which may biologically or chemically interact with the biomolecules of said solution.

3. Biosensor according to claim 1 wherein the substrate is made of a material selected from the group consisting of silicon, glass, plastic, and oxide compounds.

4. An array comprising more than one biosensor as defined in claim 1, each biosensor being fixed on a common support.

5. An assembly consisting of one or more biosensors as defined in claim 1 and comprising optical means for excitation and detection.

6. The assembly according to claim 5 wherein said optical means is a fluorescence measurement unit comprising a detector which is a single-photon detector, an avalanche photodiode (APD), or a photomultiplier tube (PMT).

7. A method for detecting and measuring diffusion kinetics of fluorescent biomolecules and biomolecular interactions that comprises:
   a) providing at least one biosensor as defined in claim 1;
   b) filling said biosensor(s) from the lateral apertures by depositing onto the biosensor(s) an aqueous solution containing fluorescent biomolecules;
   c) placing an optical system, protected by a contamination filter if in contact with said aqueous solution;
   d) determining the presence and the diffusion kinetics of fluorescent biomolecules and those passing through an optical detection volume which can be partly or totally confined inside said nanoslit.

8. Method according to claim 7 wherein said biomolecules are proteins, DNA, RNA, antibodies, amino acids, nucleic acids, enzymes, lipid molecules, polysaccharides or virus.

9. Method according to claim 7 wherein said aqueous solution also may serve as liquid usually used with liquid immersion objectives.

10. The biosensor according to claim 2 wherein the substance is biomolecules.

11. The assembly according to claim 6 wherein the single-photon detector is a detector array.

12. A biosensor for detecting and measuring interactions of fluorescently labeled biomolecules, said biosensor consisting essentially of a substrate having an upper part designed to be located in front of an optical system, a lower part, and at least two lateral apertures having a specific design, said biosensor further comprising a space for a solution containing biomolecules,
wherein said space is a nanoslit which is defined between said upper part and lower part and which communicates with the lateral apertures, wherein the at least two lateral apertures have an area from 100 $nm^2$ to 20 $mm^2$ and the nanoslit has a height between 2 nm and 1000 nm, a width between 2 nm and 20 mm, and a length between 2 nm and 20 mm, and wherein the design of the at least two lateral apertures comprises two apertures that flank a common channel and the design allows the solution to directly enter into the nanoslit by capillarity, without being mechanically injected into the nanoslit.

13. Biosensor according to claim 12 wherein the nanoslit has internal walls, and the internal walls of the nanoslit are pre-coated with a substance, which may biologically or chemically interact with the biomolecules of said solution.

14. Biosensor according to claim 12 wherein the substrate is made of a material selected from the group consisting of silicon, glass, plastic, and oxide compounds.

15. An array comprising more than one biosensor as defined in claim 12, each biosensor being fixed on a common support.

16. An assembly consisting of one or more biosensors as defined in claim 12 and comprising optical means for excitation and detection.

17. The assembly according to claim 16 wherein said optical means is a fluorescence measurement unit comprising a detector which is a single-photon detector, an avalanche photodiode (APD), or a photomultiplier tube (PMT).

18. The biosensor according to claim 13 wherein the substance is biomolecules.

19. The assembly according to claim 17 wherein the single-photon detector is a detector array.

20. A biosensor for detecting and measuring interactions of fluorescently labeled biomolecules, said biosensor consisting essentially of a substrate having an upper part designed to be located in front of an optical system, a lower part, and at least two lateral apertures having a specific design, said biosensor further comprising a space for a solution containing biomolecules,
wherein said space is a nanoslit which is defined between said upper part and lower part and which communicates with the lateral apertures, wherein the at least two lateral apertures have an area from 100 $nm^2$ to 20 $mm^2$ and the nanoslit has a height between 2 nm and 1000 nm, a width between 2 nm and 20 mm, and a length between 2 nm and 20 mm, wherein the design of the at least two lateral apertures allows the solution to directly enter into the nanoslit by capillarity, without being mechanically injected into the nanoslit, and wherein there is no structure that provides injection and negative pressure to move fluid through the biosensor.

21. Biosensor according to claim 20 wherein the nanoslit has internal walls, and the internal walls of the nanoslit are pre-coated with a substance, which may biologically or chemically interact with the biomolecules of said solution.

22. Biosensor according to claim 20 wherein the substrate is made of a material selected from the group consisting of silicon, glass, plastic, and oxide compounds.

* * * * *